United States Patent
Konchitsky

(10) Patent No.: US 7,548,779 B2
(45) Date of Patent: Jun. 16, 2009

(54) MICROWAVE ENERGY HEAD THERAPY

(76) Inventor: Alon Konchitsky, 20488 Stevens Creek Blvd., #1402, Cupertino, CA (US) 95014

(*) Notice: Subject to any disclaimer, the term of this patent is extended or adjusted under 35 U.S.C. 154(b) by 457 days.

(21) Appl. No.: 11/164,220

(22) Filed: Nov. 15, 2005

(65) Prior Publication Data

US 2007/0112392 A1    May 17, 2007

(51) Int. Cl.
*A61N 1/00* (2006.01)
(52) U.S. Cl. .................. 607/2; 607/45; 607/46
(58) Field of Classification Search ......... 607/154–156, 607/2, 45, 46, 101
See application file for complete search history.

(56) References Cited

U.S. PATENT DOCUMENTS

| | | | | |
|---|---|---|---|---|
| 4,344,440 A | | 8/1982 | Aaby et al. .................. 128/653 |
| 4,621,642 A | | 11/1986 | Chen .......................... 128/422 |
| 4,800,899 A | | 1/1989 | Elliott ......................... 128/804 |
| 4,858,612 A | * | 8/1989 | Stocklin ....................... 607/45 |
| 5,131,409 A | | 7/1992 | Lobarev et al. ............. 128/804 |
| 5,152,286 A | * | 10/1992 | Sitko et al. ................... 607/45 |
| 5,317,155 A | * | 5/1994 | King ........................... 250/324 |
| 5,342,410 A | | 8/1994 | Braverman ................. 607/58 |
| 5,411,540 A | | 5/1995 | Edell et al. .................. 607/53 |
| 5,418,372 A | | 5/1995 | Schonberg et al. ........ 250/492.3 |
| 5,481,196 A | * | 1/1996 | Nosov ......................... 324/637 |
| 5,507,791 A | * | 4/1996 | Sit'ko .......................... 607/101 |
| 5,718,721 A | * | 2/1998 | Ross ........................... 607/46 |
| 5,983,141 A | * | 11/1999 | Sluijter et al. ............... 607/100 |
| 6,067,475 A | | 5/2000 | Graves et al. ............... 607/101 |
| 6,122,550 A | * | 9/2000 | Kozhemiakin et al. ...... 607/101 |
| 6,167,304 A | * | 12/2000 | Loos ............................. 607/2 |
| 6,233,479 B1 | | 5/2001 | Haddad et al. .............. 600/430 |
| 6,434,423 B1 | | 8/2002 | Ross ............................. 607/2 |
| 6,451,014 B1 | | 9/2002 | Wakikaido et al. ........... 606/33 |
| 6,454,711 B1 | | 9/2002 | Haddad et al. .............. 600/371 |
| 6,839,589 B2 | | 1/2005 | Petlan ........................... 607/2 |
| 6,873,872 B2 | | 3/2005 | Gluckman et al. ............ 607/2 |
| 2005/0107853 A1 | | 5/2005 | Krespi et al. | |
| 2005/0203578 A1 | * | 9/2005 | Weiner et al. .................. 607/2 |

* cited by examiner

*Primary Examiner*—Scott M Getzow
(74) *Attorney, Agent, or Firm*—Carla L. Gannon

(57) ABSTRACT

A therapy whereby high frequency electromagnetic pulses are externally applied to a head. The microwave signals effectively resynchronize neural firings thereby lessening or curing certain conditions such as headaches, depression, migraines and auras associated with migraines and epilepsy. The preferred frequency is 3-100 GHz (3,000-100,000 MHz) and the preferred duration of pulses is 1 microsecond-3 seconds. The therapeutic variables include frequency of wavelength, duration of pulse administration, area or areas of head targeted, power of waves and angle of wave application.

8 Claims, 3 Drawing Sheets

MICROWAVE ENERGY HEAD THERAPY

FIELD OF INVENTION

This invention relates to a therapy whereby high frequency electromagnetic pulses are externally applied to a head to resynchronize neural firings and lessen or cure certain conditions such as headaches, depression, migraines and auras associated with migraines and epilepsy.

DESCRIPTION OF RELATED ART

Research points to an electrical basis for some pathological conditions. For example, during the early or aura stage of a migraine headache there is a phenomenon of spreading depression which travels over the brain. Abnormal brain electrical patterns also exist in patients with epilepsy and depression.

Seizures, for example, are uncontrollable discharges of neurons. These discharges can involve only a small part of the brain, or can be on both cerebral hemispheres. Sometimes a partial seizure, or one involving only part of the brain, can spread to the whole brain. In the case of seizures, people often know they are about to have a seizure because they see or hear something, or feel dizzy, nauseous, or "strange." This is called an aura. Auras often act as an "early warning system" telling a person that a seizure is about to happen.

The electrical basis for pathological conditions is likely to be identified in many more disorders as researchers continue probing the link.

It is known that physically, every conductive material can behave like antenna in a specific wavelength. The brain is capable of acting as an antenna, or receiving energy, at certain wavelengths. When the brain receives electromagnetic energy, it causes charges and discharges in the area.

The present invention makes use of the brain's antenna characteristic. It is based on the premise that charges and discharges applied to the brain will result in an equal distribution of energy in the area, thereby effectively resetting or resynchronizing the neuronal firings. In essence, the present invention is akin to a cardiac pacemaker insofar as they both employ electrical signals to normalize physiological functions.

The use of microwave energy is not new in the medical field. In particular, microwaves have been used in diagnostics, as well as methods and devices for therapy. The patents below were selected for discussion because they either claim a method or device employing microwaves administered similarly to the present invention for a non-therapy, or claim an actual microwave therapy.

U.S. Pat. No. 4,621,642 to Chen describes an apparatus for applying microwaves within a range of 100-3,000 MHz to certain points on the body defined by traditional Chinese medicine. It is believed that health may be improved by regulating the human's electromagnetic field. This device is an improvement over existing microwave therapy employed in acupuncture therapy insofar as a needle is not required, thereby lessening discomfort and fear in patients. The present invention overcomes the limitations of the patented invention in that the present invention is used on the head in general, and is not limited to specific points. Moreover, the patented invention discloses using frequencies in the 100-3,000 MHz range, which are not fast enough for the brain receptors to receive the energy charges, and desired therapeutic effect. The frequencies employed in the present invention are those which are received by brain receptors.

U.S. Pat. No. 5,342,410 to Braverman describes a device for, and method of applying an electrical signal with 50-300 Hz frequency to humans. The invention is designed to increase the amplitude of P300 waves in the brain, with the intended benefit of decreasing interest in drugs and alcohol. It is believed that since patients with low P300 wave activity crave drugs and alcohol, increasing the activity will lessen the cravings. The patented invention differs from the present invention with respect with respect to wave frequency (0.1 to 400 Hz versus 3,000 to 100,000 MHz), where pulse is applied (forehead and wrist area versus head), and the actual pulse width (0.2 to 2 milliseconds versus 1 microsecond to several seconds).

U.S. Pat. No. 5,411,540 to Edell et al. describes a device and method for stimulating neurons. It is based on the idea that neural tissue may be stimulated via the axons or soma, and that selective excitation is necessary to achieve the desired effect. The patent sets forth axon and soma stimulation profiles, and a device for applying the pulses to excite each. The patented invention differs from the present invention in that the patented invention uses frequencies (0 to 4 KHz versus 3,000-50,000 MHz), selectively stimulates neural tissue by different pulse profiles and considers the geometry of the placement of the electrodes (or antennae) based on the subcellular structure.

U.S. Pat. No. 6,167,304 to Loos describes an apparatus and method of nervous system manipulation using external electrical pulses. The invention uses weak signals, such that classical nerve stimulation does not occur. Pulses are administered with variability so as to prevent nervous system habituation, avoid need for precise resonance tuning, and to control certain pathologies, The present and patented inventions are different in that the patented invention uses 0.5 to 2.4 Hz pulses to modulate afferent nerves, versus 3,000 to 50,000 MHz pulses, to create an action potential within the brain. Also, the present invention does necessarily not introduce variability in the pulse pattern.

U.S. Pat. No. 6,434,423 B1 to Ross describes method for reducing or eliminating migraine headaches. The migraine headache therapeutic benefit is derived by applying microwaves to blood so that the blood cells assume a "pearl chain" formation, thereby increasing blood flow or velocity. The patented invention differs from the present invention in that the patented invention applies the microwaves to a part of the body, preferably near an artery, which is remote from the brain. Moreover, the frequencies are different (preferably around 27.17 MHz for the patented invention versus 3,000 to 50,000 MHz for the present invention). Finally, the mechanisms of action differ (formation of "pearl chain" to increase blood flow versus changing action potential).

U.S. Pat. No. 6,454,711 B1 to Haddad et al. describes a device and method which employs microwave signals to detect hemorrhagic activity in a brain or pleural cavity. It is easier and cheaper than traditional CAT scan technology and may be used in the field where time is of the essence. The patent teaches applying a pulse of 2-5 GHz directly to the brain for diagnostic purposes.

U.S. Pat. No. 6,839,589 B2 to Petlan describes a device and method for human, plant and animal electrotherapy. The living organism is placed near the antennae, electromagnetic pulses are applied and the organism's resonant frequency is determined. Based on the resonant frequency and desired effect, the subject is exposed to electromagnetic pulses at a determined frequency for a determined amount of time. The present invention and the patented invention are dissimilar in that the patented invention does not limit electromagnetic force application to the brain, the frequencies are different (10-50 MHz, preferably 18-18.5 MHz, versus 3,000-50,000 MHz), the targeted disorders are different and the present therapy does not require determining the organism's resonant frequency.

U.S. Pat. No. 6,873,872 B2 to Gluckman et al. describes a device and method for modifying neural activity in vivo, in vitro or in situ. It essentially covers placing an electrode directly into the tissue and applying the desired field. The present invention and the patented invention are dissimilar in that the patented invention delivers the electromagnetic force internally and uses field below what would cause 100% action potential. Also, the frequency of the patented device is below 10 Hz.

SUMMARY OF THE INVENTION

The MICROWAVE ENERGY HEAD THERAPY is a method of therapy for any disorder which is caused by abnormal electrical charges and discharges in the brain. The therapy involves administering high frequency electromagnetic pulses, or microwaves, to a patient in varying frequencies, durations, areas, powers and angles.

The brain, either human or non-human, can be viewed as an organic circuit system. It has various parts which transmit messages via electrical signals to other parts. Similar to a computer or other circuit system, misfirings can be problematic. In a computer it could result in a sudden inability of the computer to perform a basic function. In the case of a brain, misfirings can result in pathological conditions for the organism such as migraines, and/or epilepsy.

Inorganic circuits (like in a computer) and organic circuits (like neurons in a brain) differ in a very important way, though. Whereas the electrical source in an inorganic circuit originates at the power source, the power source in an organic circuit lies within each cell. This is based on the individual neuron's ability to cause action potentials through calcium channels and other subcellular mechanisms.

This distinction is important because it suggests that the electrical flow of the whole can be affected by targeting groups of cells. In the same way that a cardiac pacemaker creates an action potential and causes the heart muscle to rhythmically contract, an electromagnetic force creates an action potential and causes neurons to fire. When misfiring neurons can be normalized, pathological conditions can be lessened or cured.

In the present invention microwave energy is administered by an external device with adjustable power, frequency, angle of emission and pulse duration. The treatment itself involves administrating the pulses at a specific power, frequency, angle and pulse duration and treatment duration to one or more sections of the head. The section of the head receiving the microwave energy depends on the area of the brain responsible for the pathology.

BRIEF DESCRIPTION OF THE DRAWINGS

The invention will be better understood by a Detailed Description of the Preferred Embodiment, when read in reference to the drawings, in which.

DETAILED DESCRIPTION OF THE PREFERRED EMBODIMENT

Figure 1:
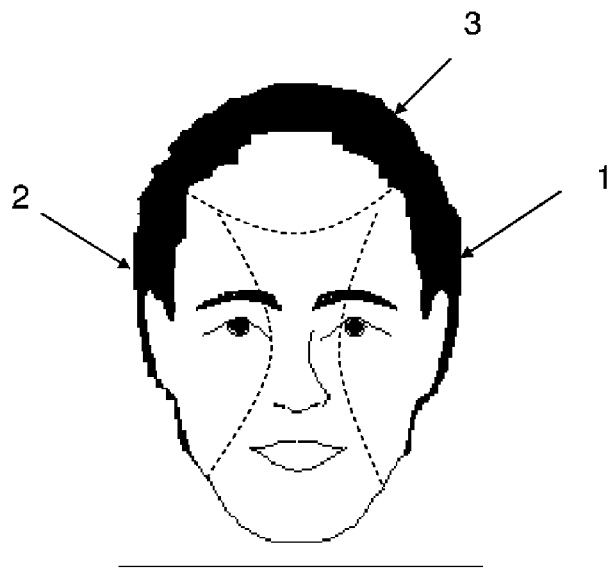
FIG. 1 is a sectional view of the left, right and top portions of the head.
Figure 2:
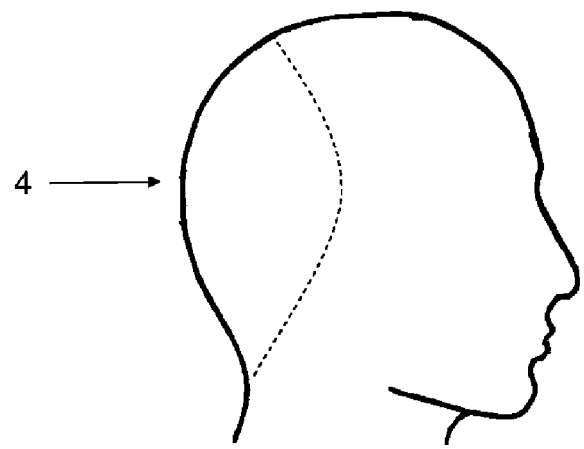
FIG. 2 is a sectional view of the back portion of the head.

Referring now to the drawings, wherein like numerals reflect like elements throughout the various figures:

FIG. 1 shows the right (1), left (2) and top (3) portions of the head and FIG. 2 shows the back of the head (4). Dividing the head into general regions is necessary because the location of the microwave energy application will vary according to the therapy desired. For example, electrical disturbances (spreading depression) are often detected in the cortex region of the brain preceding a migraine headache. The cortex region of the brain is found in the upper portion of the head. Thus, the microwave head therapy for migraine prevention can be the application of microwaves to the upper front, back or side portions of the head.

It will be understood by persons of ordinary skill in the art that the exact location and physical extent of electrical disturbances may vary between people, and even between episodes in the same person, depending on the specific pathology and severity of episode. Thus, if the therapeutic effect is not achieved upon administration to the presumed therapeutic target, another portion of the head should be tried. The goal is resynchronization of the neural firings, and it may be necessary to try different parts of the head, and different angles, so the affected area receives the desired energy.

Figure 3:
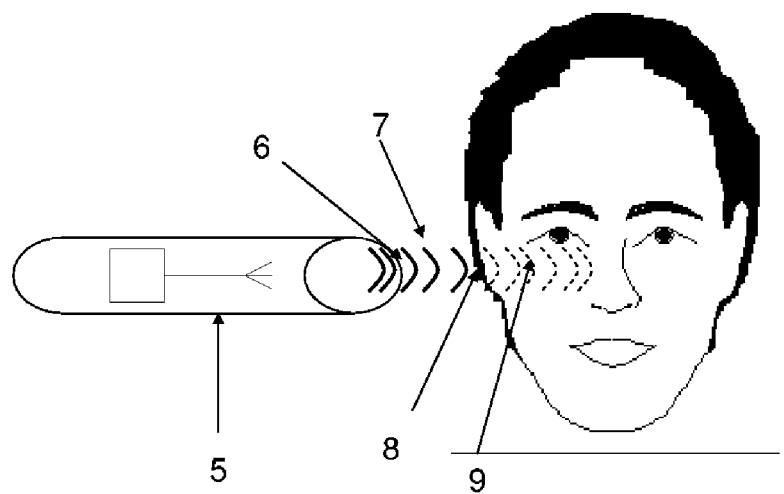
FIG. 3 is view the microwave generating device applying microwave energy to a localized portion on the right side of the head.

FIG. 3 shows a microwave generating device (5) emitting microwave energy, with a portion through which the electromagnetic waves are emitted (6) directed to an external portion of the head (8) and resulting in microwave energy being transmitted into the head (9).

The microwave generating device (5) must be adjustable with respect to power, frequency, pulse duration and angle of emission. The preferred power is can vary from 0 dBm to 45 dBm, the preferred frequency is 3-100 GHz (3,000-100,000 MHz), the preferred duration of pulses is 1 microsecond-3 seconds, the preferred duty cycle of 1% to 50% and the preferred ranges of angle emission is 1 to 180 degrees.

The portion of the device where the electromagnetic waves are emitted (6) should be suitable for positioning in close proximity to the subject's head. For example, it should not have irregularly protruding or sharp parts that create a hazard or impracticality for therapeutic uses. In addition, the electromagnetic wave emitting portion should either be maneuverable, or mounted such that a subject may easily position themselves to receive the pulses.

Microwaves are spherically emitted from antennae. In other words, when microwaves are generated they form a ball of microwave energy around the source, as opposed to a beam. In order to direct the microwaves in the desired location some waves from the sphere are impeded while others flow freely. The mechanism of controlling the flow of the microwaves is the opening of the microwave generating device (6). The angle or size of the opening (6) should also be adjustable so that different volumes of waves are emitted. For example, where a specific therapy requires a focused beam of microwaves to a distinct part of the head, the opening (6)

should be small. Alternatively, where a therapy requires the generalized application of microwaves to a large region of the brain, the opening (6) should be large.

Figure 4:
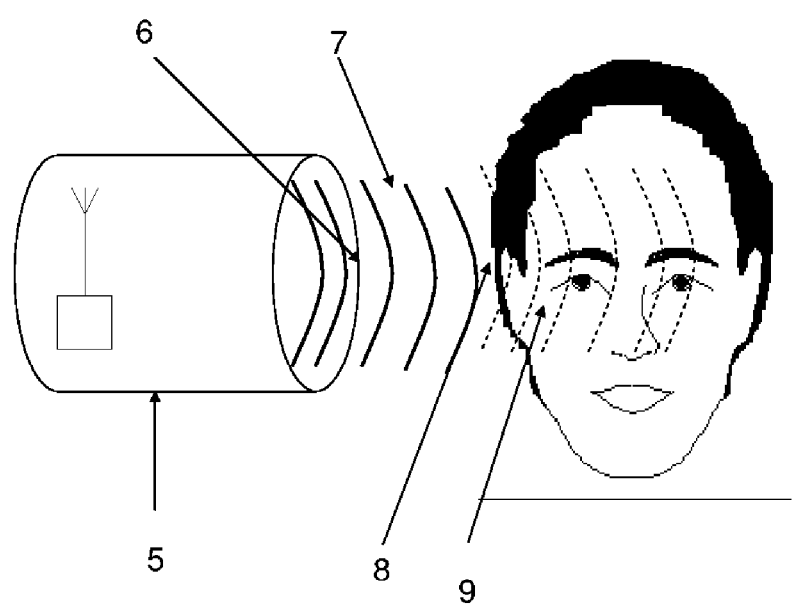
FIG. 4 is a view of the microwave generating device applying microwave energy to a generalized region on the right portion of the head.

The effect of a relatively small opening (6) resulting in a relatively focused microwave emission (7) is exemplified in FIG. 3. In contrast, FIG. 4 shows a relatively large opening (6) resulting in a relatively generalized microwave emission (7).

As expected, the extent of microwaves transmitted into the brain (9) is related to the extent of the microwaves emitted from the device (7) and contacting the external portion of the head (8).

To summarize, the microwave generating device (5) emits a sphere of microwave energy. The size of the opening of the device (6) determines the volume of the microwave sphere that flows from the device. The microwaves flowing from the device (7) are directed to an external portion of the head (8). Microwaves transmitted into the brain (9) cause a therapeutic effect by essentially resynchronizing neural firings.

Figure 5:
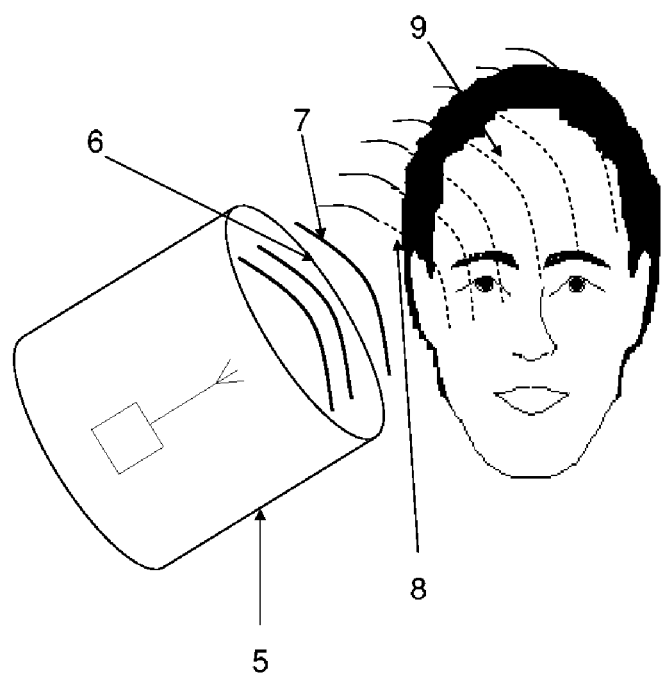
FIG. 5 is a view of the microwave generating device applying microwave energy at an angle, thereby delivering energy to the right and top portions of the head simultaneously.

FIG. 5 depicts the microwave generating device (5) aimed at the head at an angle, so that multiple regions of the head are receiving microwave energy simultaneously. This is to illustrate that the regions of the head exemplified in FIGS. 1 and 2 need not be treated separately. Microwave energy may be applied in any therapeutically useful manner.

The device should be adjustable so the operator may quickly and easily change therapeutic parameters such as power, frequency and pulse duration. The device should be easy to operate and should include safety devices so that the subject does not accidentally receive hazardous microwave energy. The device should contain an emergency shut-off switch in the event the therapy should be immediately stopped. Finally, the device should contain a recording device, such as running tape, so that the parameters, and operator's comments, can be recorded during therapy.

Figure 6:
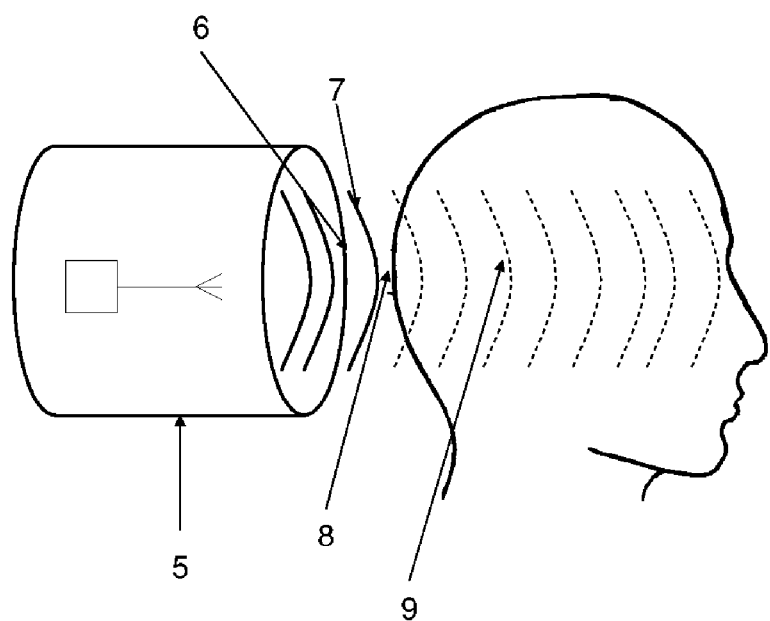
FIG. 6 is a view of the microwave generating device applying microwave energy to a generalized region on the back portion of the head.

FIG. 6 depicts therapy directed towards the back region (4) of the head.

The specific region of the head to be targeted requires both directed and spontaneous therapeutic methods, and keen observation. Where the organic origin of a disorder is known, for example the specific location of electrical disturbances associated with an epileptic seizure, the therapy should be initially directed to that region. The subject should be observed for subjective and objective indications of improvement. For example, the subject should be asked to rate pain, or presence or absence of aura, prior to and immediately following microwave application. Subject brain activity can be monitored by electrodes in addition to, or instead of subjective information.

If no improvement is noted, parameters such as power, frequency and pulse duration should be individually and incrementally adjusted until improvement is noted. This may be achieved by sweeping from 3-100 GHz for range finding purposes, then fine tuning as appropriate. If treatment of the region does not cause improvement of the condition, the region of treatment should be expanded.

The subject should be treated until improvement is noted, or detrimental effects of the therapy are observed. Treatments should be repeated until sustained improvement is achieved, or for maintenance where improvement does not appear sustainable.

In the case of migraine and epilepsy treatment, the patient would preferably be treated immediately after first perceiving an aura. If the neural firings are resynchronized during the "early warning" stage, the more harmful and unpleasant progressive manifestations, namely migraine headache and epileptic seizure, may be avoided.

When a therapeutic effect is achieved, data related to the parameters of the therapeutic protocol should be saved and preferably entered into a database available to others who use the invention at issue.

While the preferred embodiment of the invention has been depicted in detail, modification and adaptations may be made thereto without departing from the spirit and scope of the invention as shown in the following claims:

What is claimed is:

1. A method of treating a neural electrophysical pathology using a microwave generating device, said method comprising the nonsequential steps of:
adjusting the power of said device to a value between about 0 dBm and about 45 dBm;
adjusting the frequency of said device;
adjusting the pulse duration of said device;
adjusting the duty cycle of said device; and
adjusting the range of emission of said device;
sequentially followed by remotely positioning said device in close proximity to a subject's head and emitting microwaves from said device.

2. The method of claim 1 wherein said step of adjusting the frequency comprises the step of adjusting the frequency to a value between about 3 GHz and about 39 GHz.

3. The method of claim 1 wherein said step of adjusting the frequency comprises the step of adjusting the frequency to a value between about 71 GHz and about 100 GHz.

4. The method of claim 1 wherein said step of adjusting the pulse duration comprises the step of adjusting the pulse duration to a value between about 1 microsecond and about 3 microseconds.

5. The method of claim 1 wherein said step of adjusting the duty cycle comprises the step of adjusting the duty cycle to a value between about 1% and about 50%.

6. The method of claim 1 wherein said step of adjusting the range of emission comprises the step of adjusting the range of emission to a value between about 1 degree and about 180 degrees relative to the subject's head.

7. The method of claim 1 wherein said neural electrophysical pathology is selected from the group consisting of headaches, depression, migraine headaches, epilepsy, auras associated with migraine headaches and auras associated with epilepsy.

8. The method of claim 1 further comprising the step of initiating the treatment immediately after subject's perception of an aura.

* * * * *